(12) United States Patent
Dal Farra et al.

(10) Patent No.: US 9,029,329 B2
(45) Date of Patent: May 12, 2015

(54) CASPASE-14 ACTIVATOR PEPTIDES AND COMPOSITIONS COMPRISING SAID PEPTIDES

(75) Inventors: Claude Dal Farra, Kerhonkson, NY (US); Nouha Domloge, Valbonne (FR); Jean-Marie Botto, Valborne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/576,938

(22) PCT Filed: Feb. 1, 2011

(86) PCT No.: PCT/FR2011/000060
§ 371 (c)(1),
(2), (4) Date: Aug. 2, 2012

(87) PCT Pub. No.: WO2011/095705
PCT Pub. Date: Aug. 11, 2011

(65) Prior Publication Data
US 2013/0121935 A1  May 16, 2013

(30) Foreign Application Priority Data
Feb. 5, 2010  (FR) ..................................... 10 00463

(51) Int. Cl.
| A61K 8/64 | (2006.01) |
| A61K 38/08 | (2006.01) |
| A61Q 19/00 | (2006.01) |
| C07K 7/06 | (2006.01) |
| A61Q 19/08 | (2006.01) |
| A61Q 17/04 | (2006.01) |
| A61K 38/00 | (2006.01) |

(52) U.S. Cl.
CPC . *A61K 8/64* (2013.01); *A61K 38/00* (2013.01); *A61Q 19/08* (2013.01); *A61Q 17/04* (2013.01); *A61Q 19/004* (2013.01)

(58) Field of Classification Search
CPC ....... A61K 8/64; A61K 38/00; A61Q 19/004; A61Q 17/04; A61Q 19/08
See application file for complete search history.

(56) References Cited

U.S. PATENT DOCUMENTS

| 5,516,507 | A | * | 5/1996 | N'Guyen et al. ................ 424/59 |
| 5,560,917 | A | | 10/1996 | Cohen et al. |
| 5,770,687 | A | | 6/1998 | Hornik et al. |
| 5,820,850 | A | | 10/1998 | Hashimoto et al. |
| 5,837,218 | A | * | 11/1998 | Peers et al. ................... 424/1.69 |
| 5,853,705 | A | | 12/1998 | Naitoh et al. |
| 6,117,974 | A | | 9/2000 | Gilon et al. |
| 6,399,083 | B1 | | 6/2002 | Pillai et al. |
| 2002/0106404 | A1 | * | 8/2002 | Lipton .......................... 424/450 |
| 2002/0123522 | A1 | * | 9/2002 | Fritz et al. ..................... 514/419 |
| 2005/0271650 | A1 | * | 12/2005 | Freimark et al. ........... 424/130.1 |
| 2013/0210743 | A1 | | 8/2013 | Guerlavais et al. |

FOREIGN PATENT DOCUMENTS

| WO | WO 97/35876 A1 * | 10/1997 | ............... C07K 7/00 |
| WO | WO/02/081027 | 10/2002 | |
| WO | WO/2004/084646 | 12/2005 | |
| WO | WO/2006/020164 | 2/2006 | |
| WO | WO/2009/106343 | 9/2009 | |

OTHER PUBLICATIONS

Wrinkles Treatment & Advice, from http://www.drbaileyskincare.com/wrinkle-treatment.shtml, pp. 1-5, accessed Jun. 21, 2013.*
Sunscreen: How to Select, Apply, and Use It Correctly, from http://www.cdc.gov/mmwr/preview/mmwrhtml/rr5104a3.htm, pp. 1-2, accessed Jun. 21, 2013.*
Physical Changes with Aging, from Merck Manual, pp. 1-4. accessed Oct. 15, 2012.*
Bont et al, Endogenous DNA damage in humans: a review of quantitative data, Mutagenesis, 2004, 19, pp. 169-185.*
Sinha et al, UV-induced DNA damage and repair: a review, Photochem. Photobiol. Sci., 2002, 1, pp. 225-236.*
Common foods cause DNA damage, from http://www.biosciencetechnology.com/news/2013/03/common-foods-cause-dna-damage, pp. 1-10, accessed Jun. 21, 2013.*
Ames, Micronutrient Deficiencies: A Major Cause of DNA Damage, from http://onlinelibrary.wiley.com/doi/10.1111/j.1749-6632.1999.tb08727.x/abstract;jsessionid..., pages 1-2, accessed Jun. 21, 2013.*
Kayalar et al, Cleavage of actin by interleukin 1beta-converting enzyme to reverse DNase I inhibition, Proc. Natl. Acad. Sci. USA, 1996, 93, pp. 2234-2238.*

* cited by examiner

*Primary Examiner* — Julie Ha
*Assistant Examiner* — Li Ni Komatsu
(74) *Attorney, Agent, or Firm* — Thompson Hine LLP

(57) ABSTRACT

The invention relates to peptidic compounds of general formula (I) $R_1-(AA)_n-X_1-X_2\text{-Ile-Gln-Ala-Cys-Arg-Gly-}X_3-(AA)_p-R_2$ as caspase-14 activators. The invention also relates to a cosmetic or pharmaceutical composition comprising at least one peptide of general formula (I), in a physiologically acceptable medium, and to the use of said composition for preventing and/or repairing damage to deoxyribonucleic acid, for preventing and/or treating cutaneous signs of ageing and photo-ageing, and for improving the skin barrier function. The invention further relates to a cosmetic treatment method for preventing and/or treating cutaneous signs of ageing and photo-ageing, and for preventing and/or repairing damage caused by ultraviolet radiation.

8 Claims, 2 Drawing Sheets

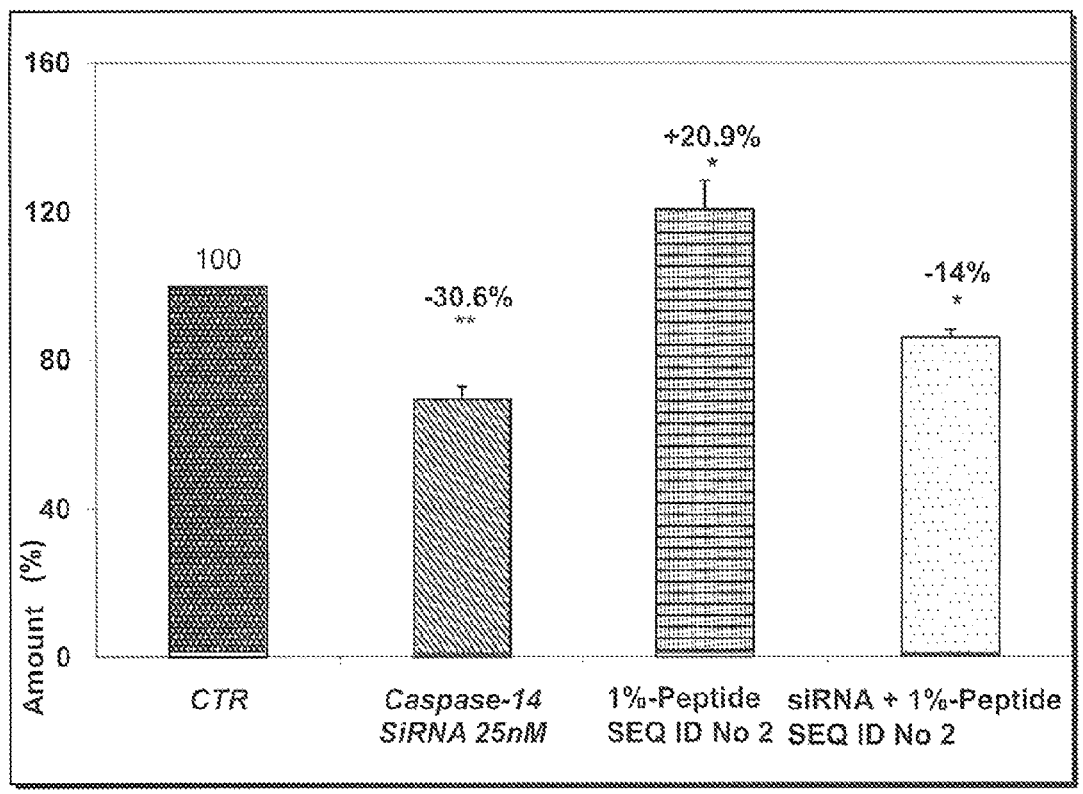
Fig. 1: Quantification of caspase-14 in NHK cells transfected with a siRNA/caspase-14 gene and treated with a peptide SEQ ID No2

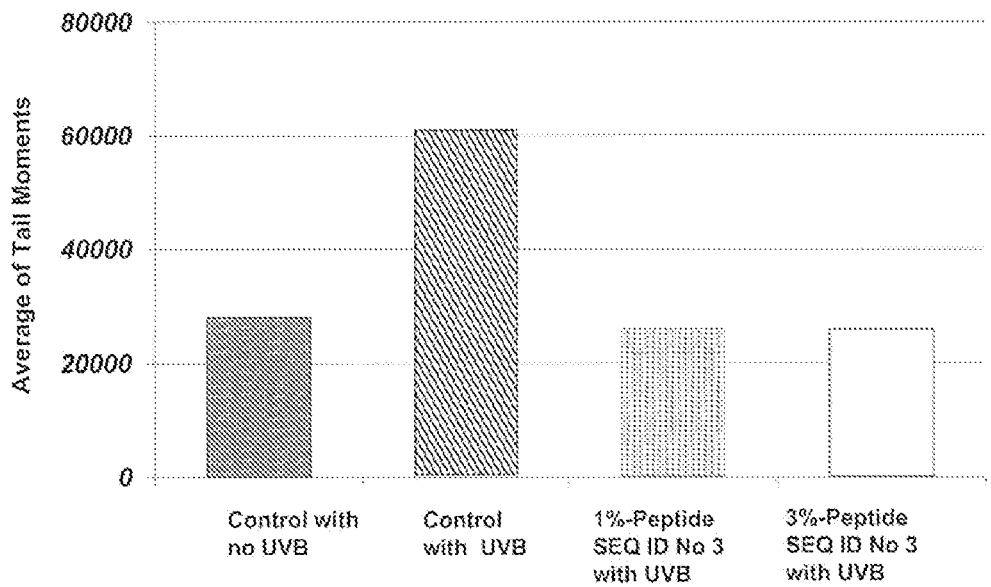
Fig. 2a: Comets test on NHK cells treated or not with peptide SEQ ID No 3 and then subjected to UVB radiation (protective effect of the peptide)
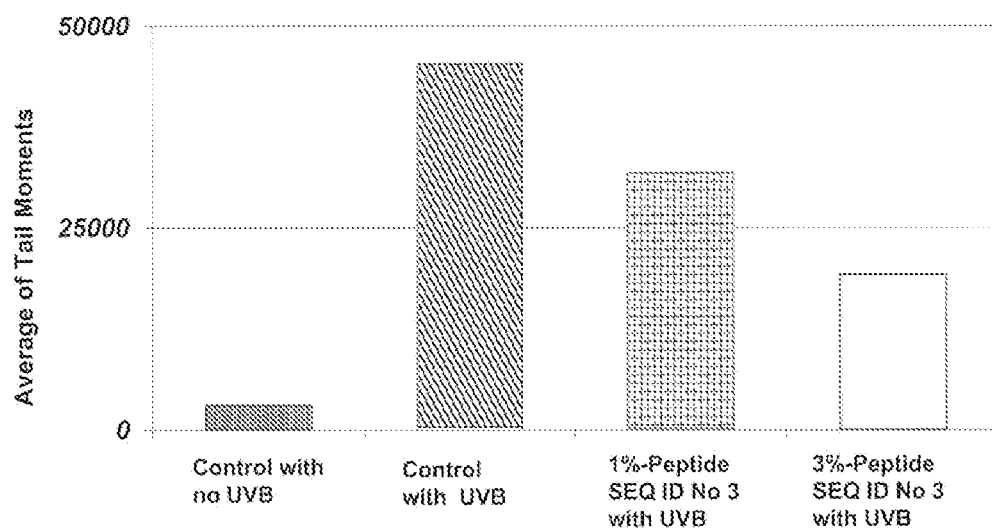
Fig. 2b: Comets test on NHK cells subjected to UVB radiation and then treated or not with peptide SEQ ID No 3 (repairing effect of the peptide)

CASPASE-14 ACTIVATOR PEPTIDES AND COMPOSITIONS COMPRISING SAID PEPTIDES

CROSS REFERENCE TO RELATED APPLICATIONS

This application is the national stage of PCT Application No. PCT/FR2010/000060 filed Feb. 1, 2011, which claims priority from French Patent Application No. 1000463, filed Feb. 5, 2010, the entire disclosures of which are hereby incorporated in their entirety.

The present invention pertains to the cosmetic and pharmaceutical fields. It relates to peptide compounds of the following general formula (I): $R_1$-$(AA)_n$-$X_1$-$X_2$-Ile-Gln-Ala-Cys-Arg-Gly-$X_3$-$(AA)_p$-$R_2$, as caspase-14 activators, and to their use in cosmetics and/or pharmaceutics in order to prevent and/or correct damage caused to deoxyribonucleic acid (DNA), prevent and/or treat the signs of skin aging and photoaging and improve the skin barrier function.

The main function of the skin, which is the largest organ in the human body, is to protect the latter against many forms of aggression, including external aggressions. Examples of these include aggressions such as pollution, UV ultraviolet (UV) radiation, or also irritating chemicals such as surfactants, preservatives or perfumes, mechanical aggressions such as abrasion, shaving or depilation. By pollution, are meant both "external" pollution, for example due to diesel particles, ozone, or heavy metals, and "internal" pollution, which may be due in particular to solvents released by paints, glues or wallpapers (such as toluene, styrene, xylene, or benzaldehyde), or also cigarette smoke. Dryness of the atmosphere is also a major cause of cutaneous aggression. Such external aggressions lead to an alteration of the skin barrier function, which results in skin discomfort, unpleasant sensory phenomena, such as tightness or itching, or even excessive fragility and redness. In addition, these external aggressions contribute to the acceleration of so-called "extrinsic" aging of the skin. Indeed, extrinsic aging is caused by environmental factors to which the body is subjected throughout its life, which factors are collectively referred to as external aggressions.

In addition to its role as a physical barrier, the skin acts as a water-impervious barrier in order to prevent dehydration. This barrier formed by the skin is made of several layers composed of cells of various types that ensure the skin's continuous renewal. This renewal process involves, above all, a phenomenon in which the superficial cells of the skin desquamate, which phenomenon must be compensated for by renewal of the epidermis ensured by the keratinocytes in the basal layer, which actively divide and differentiate into cells of the stratum corneum, or corneocytes. These renewing, and also skin repairing actions in the case of damage such as UV-radiation induced damage, are highly controlled by a set of signaling pathways. One of these signaling pathways involves a protease, caspase-14. Caspase-14 is a unique member of the caspase family. Indeed, unlike other members of the ubiquitously expressed caspase family, caspase-14 is expressed and active only in the epidermis and is nonexistent in most other adult tissues (Eckhart et al., *J. Invest. Dermatol.*, 2003, 44:1148-1151). The crucial role of caspase-14 in the formation of the barrier constituted by the epidermis has recently been demonstrated (Denecker et al., *Nat. Cell. Biol.* 2007, 9:666-674). Indeed, it is expressed and exerts its proteolytic action only within those layers of the epidermis where differentiation and "cornification" take place, as well as in the hair follicle (Lippens et al., *Cell Death Differ.*, 2000, 10:257-259). However, it has been shown that caspase-14 plays a significant role, in particular in the maintenance of the processes of hydration, corneocyte formation, and apoptosis protection, in particular in the case of external aggressions such as those due to UV radiation (Denecker et al., *J. Cell Biology*, 2008, 451-458). Moreover, it has been shown that caspase-14 is responsible for the cleavage of profilaggrin into filaggrin, which filaggrin is then hydrolyzed into peptides and amino acids, which form the Natural Moisturizing Factor (Hoste et al., *J. Invest. Dermatol. Abstract*, 2007, S71). All of these conclusions have led, amongst other things, to the development of pharmaceutical compositions comprising caspase-14 as the active ingredient, which can be used as a sunscreen (WO 2008025830). However, there is no cosmetic compound presently available allowing caspase-14, and thereby, the conversion of profilaggrin into filaggrin to be activated, in order to protect the skin against UV radiation, and improve the barrier function, although the need for this type of innovative care does exist.

Now, the Applicant has demonstrated that peptide compounds of the following general formula (I):

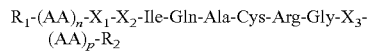

are excellent caspase-14 activator agents, and have a significant action on the improvement of the skin barrier function, as well as on the protection of the skin against external aggressions such as UV radiation, in particular thanks to a DNA protective function.

The peptide compounds according to the present invention are characterized in that they:
- activate caspase-14 and consequently, activate its proteolytic action with respect to profilaggrin;
- help preserve hydration of the epidermis;
- prevent and repair damage caused to the DNA of skin cells subjected to ultraviolet B (UVB) radiation; and
- optimize the barrier function of the epidermis.

Thus, a first object of the present invention is to provide a peptide compound of the following general formula (I):

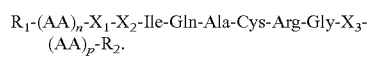

A second object of the present invention is to provide a cosmetic composition comprising as the main active ingredient said peptide compound of formula (I).

Furthermore, a third object of the present invention relates to the use a cosmetic composition comprising said peptide compound of formula (I) for (i) protecting and/or repairing the damage caused to DNA, activating caspase-14 as well as filaggrin formation, (ii) preventing and/or treating the signs of skin aging and photo-aging, and (iii) improving the skin barrier function as well as epidermis hydration.

Lastly, a fourth object of the present invention is to provide a method for the cosmetic treatment of skin or keratinous appendages to be treated, using the composition comprising said peptide compound of formula (I).

The first object of the present invention relates to a peptide compound of the general formula (I):

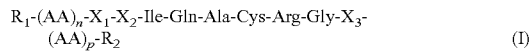

wherein
$X_1$ is an aspartic acid, glutamic acid, or no amino acid,
$X_2$ is an asparagine, a proline, a serine, or no amino acid,
$X_3$ is an asparagine, an arginine, a leucine, or no amino acid,
AA is any amino acid, and n and p are integers between 0 and 2,
$R_1$ is the free N-terminal amino acid's primary amine function, $R_2$ is the hydroxyl group of the C-terminal amino acid's carboxyl function, substituted with a group that can be selected from a $C_1$ to $C_{30}$ alkyl chain, or a $NH_2$, NHY or NYY group, where Y is a $C_1$ to $C_4$ alkyl chain, said sequence of general formula (I) comprising between 6 and 13 amino acid residues.

The term "peptide compound" or "peptide" denotes a chain of two or more amino acids linked together by peptide bonds or modified peptide bonds.

By "peptide compound" or "peptide", is meant the naturally occurring or synthetic peptide according to the present invention as described above, or at least one of its fragments, whether obtained by proteolysis or synthetically, or also any naturally occurring or synthetic peptide whose sequence entirely or partially consists of the aforedescribed peptide sequence.

The amino acids constituting the peptide compound according to the present invention may be in the Levorotatory configuration, that is, L- and/or Dextrorotatory configuration, that is D-. The peptide according to the present invention can thus be in a L-, D- or DL-form.

In order to improve resistance to degradation, it may be necessary to use a protected form of the peptide according to the present invention. The form of protection must obviously be a biologically compatible form, and should be compatible with use in the fields of cosmetics and pharmacy. Preferably, to protect the N-terminal amino acid's primary amino function, substitution with a group $R_1$ of the acyl type with a $C_1$ to $C_{30}$, saturated or unsaturated alkyl chain is used, which may be selected from an acetyl group or an aromatic group. Preferably, to protect the C-terminal amino acid's carboxyl function, substitution with a group $R_2$ of the $C_1$ to $C_{30}$ alkyl chain type, or a $NH_2$, NHY or NYY group, where Y is a $C_1$ to $C_4$ alkyl chain, is used.

The peptide according to the present invention can be protected at the N-terminal end, C-terminal end or at both ends.

In a first preferred embodiment of the present invention, in the general formula (I),
$X_1$ is an aspartic acid, a glutamic acid, or no amino acid,
$X_2$ is an asparagine, a proline, a serine, or no amino acid,
$X_3$ is an asparagine, an arginine, a leucine, or no amino acid,
integer numbers n and p are equal to zero,
$R_1$ is the free N-terminal amino acid's primary amino function, $R_2$ is the hydroxyl group of the C-terminal amino acid's carboxyl function, substituted with a group that can be selected from a $C_1$ to $C_{30}$ alkyl chain, or a $NH_2$, NHY or NYY group, where Y is a $C_1$ to $C_4$ alkyl chain, said sequence of general formula (I) comprising between 6 and 9 amino acid residues.

In a second preferred embodiment, the peptide compound corresponds to one of the following formulas:

```
                                          (SEQ ID NO: 1)
Asp-Pro-Ile-Gln-Ala-Cys-Arg-Gly-NH2

(SEQ ID NO: 2)
Ile-Gln-Ala-Cys-Arg-Gly-NH2

(SEQ ID NO: 3)
Asn-Arg-Ile-Gln-Ala-Cys-Arg-Gly-NH2

(SEQ ID NO: 4)
Pro-Ile-Gln-Ala-Cys-Arg-Gly-Phe-NH2
```

The present invention also relates to homologous forms of these sequences. By "homologous", according to the present invention, is meant any peptide sequence which is identical to at least 50%, or preferably to at least 80%, and still more preferably to at least 90% of said peptide sequence, which is selected from sequences SEQ ID NO: 1 to SEQ ID NO: 4. By "peptide sequence identical to at least X %", is meant a percentage of similarity between the amino acid residues of the two sequences to be compared, obtained after optimum alignment of the two sequences. An optimum alignment is obtained using local homology algorithms such as those used in the BLAST P computer software available from the National Center for Biotechnology Information Web site.

The term "homologous" can also refer to a peptide, which differs from the sequence of a peptide of sequences SEQ ID NO: 1 to SEQ ID NO: 5 by the substitution of chemically equivalent amino acids, that is, by substituting a residue with another having the same characteristics. Conventional substitutions are thus performed between Ala, Val, Leu and Ile; between Ser and Thr; between the acid residues Asp and Glu; between Asn and Gln; and between the basic residues Lys and Arg; or between the aromatic residues Phe and Tyr.

The peptide of general formula (I) according to the present invention can be obtained either by conventional chemical synthesis (in a solid phase or liquid homogeneous phase), or by enzymatic synthesis (Kullman et al., *J. Biol. Chem.* 1980, 225, 8234), from the constituent amino acids or derivatives thereof.

The peptide according to the present invention may be naturally occurring or synthetic. Preferably, according to the present invention, the peptide is obtained by chemical synthesis.

Lastly, the active ingredient may be a single peptide, a mixture of peptides, or peptide derivatives and/or consist of derivatives of amino acids.

The peptide compound according to the present invention can be used as a medication.

According to one advantageous embodiment of the present invention, the peptide compound according to the present invention is solubilized in one or more physiologically suitable solvents, conventionally used by those skilled in the art, such as water, glycerol, ethanol, propanediol, butylene glycol, dipropylene glycol, ethoxylated or propoxylated diglycols, cyclic polyols, or any mixture of these solvents.

According to yet another advantageous embodiment of the present invention, the peptide compound according to the present invention is solubilized in a cosmetic or pharmaceutical vector such as liposomes, or adsorbed onto powdery organic polymers, mineral carriers such as talcs and bentonites, and more generally dissolved in, or fixed to any physiologically suitable vector.

The second object of the present invention relates to a cosmetic composition comprising as the active ingredient said peptide compound of general formula (I).

Preferably, the compositions according to the present invention are in a form suitable for topical application comprising a cosmetically acceptable medium. By "cosmetically acceptable", are meant media that are suitable for use in contact with the skin or human keratinous appendages, without any risk of toxicity, incompatibility, instability, allergic response, and the like. The compositions intended to be applied to the skin can be in the form of a cream, oil-in-water or water-in-oil emulsions or multiple emulsions, a solution, suspension, micro-emulsion, aqueous or anhydrous gel, serum, or also a dispersion of vesicles, a patch, spray, ointment, pomade, emulsion, colloid, milk, lotion, stick, or also of a powder, all of which are suitable for application to the skin, lips and/or keratinous appendages.

Preferably, said peptide compound is present in the composition at a concentration of between about 0.0005 and 500 ppm, preferably at a concentration of between 0.01 and 5 ppm.

Still more preferably, the composition according to the present invention further contains at least one other active ingredient, which promotes the action of said peptide compound. Examples include, without limitation, the following classes of ingredients: other active peptide agents, plant extracts, healing, anti-aging, anti-wrinkle, soothing, free-radical scavenger, and anti-UV agents, agents that stimulate dermal macromolecule synthesis or energy metabolism, hydrating, anti-bacterial, anti-fungal, anti-inflammatory agents, anesthetics, agents that modulate skin differentiation, pigmentation or depigmentation, agents that stimulate nail or hair growth, etc. Preferably, an agent with anti-wrinkle activity, such as a free-radical scavenger or antioxidant agent, or an agent that stimulates dermal macromolecule synthesis, or also an agent that stimulates energy metabolism will be used. In particular, the active ingredient is selected from vitamins, phytosterols, flavonoids, dehydroepiandrosterone (DHEA) and/or a precursor thereof or a chemical or biological derivative thereof, a metalloproteinase inhibitor or a retinoid. Additionally, additives such as solvents, thinners, dyes, sunscreens, self-tanning agents, pigments, fillers, preservatives, odor absorbers, thickeners, emulsifiers, humectants, emollients, perfumes, antioxidants, film-forming agents, chelating agents, sequestering agents, conditioners, can be added to the composition.

In all cases, the person skilled in the art will ensure that these adjuvants as well as their proportions are chosen so as not to impair the advantageous properties sought for the composition according to the present invention. For example, these adjuvants can be present in an amount between 0.01 and 20% of the total weight of the composition. When the composition according to the present invention is an emulsion, the fatty phase can represent from 5 to 80% by weight and preferably, from 5 to 50% by weight of the total weight of the composition. The emulsifiers and co-emulsifiers used in the composition are selected from those conventionally used in the field. These can be used, for example, in an amount ranging between 0.3 and 30% by weight, with respect to the total weight of the composition.

A third object of the present invention relates to the use of a composition comprising a peptide compound according to the present invention, to prevent and/or repair the damage caused to DNA, and activate caspase-14 as well as form filaggrin. By peptide compound intended to "prevent and/or repair the damage caused to DNA", is meant a biologically active peptide compound or derivative capable of repairing the damage due to photochemical reactions between the DNA bases, such as the formation of cyclobutane pyrimidine dimers. By peptide compound which "allows caspase-14 to be activated", is meant any biologically active peptide or derivative capable of increasing the amount of caspase-14, either by increasing the protein synthesis thereof (through direct or indirect modulation of gene expression), or through other biological processes, such as stabilization or non-stabilization of messenger ribonucleic acid (RNA) transcripts. By peptide compound which allows "the formation of filaggrin" to be increased, is meant any biologically active peptide or derivative capable of increasing the amount of profilaggrin converted into filaggrin, through an increase in the proteolytic activity of caspase-14 or through an increase in the amount of caspase-14. In particular, the composition according to the present invention will be used to prevent and/or repair the damage caused to DNA by external aggressions. By "external aggressions" are meant aggressions that can be caused by the environment. Examples include aggressions such as pollution, UV radiation, or also irritating chemicals such as surfactants, preservatives or perfumes, mechanical aggressions, such as abrasion, shaving or depilation. However, preferably, external aggressions consist mainly in UV radiation, in particular UVB radiation.

Another object of the present invention relates to the use of a cosmetic composition comprising said peptide compound and a cosmetically acceptable medium to prevent and/or treat signs of skin aging and photo-aging. The "signs of skin aging" include, but are not limited to, all conspicuous manifestations caused by the aging of the skin. In particular, this denotes wrinkles, deep and coarse wrinkles, fine lines, cracks, sagging of the cutaneous and sub-cutaneous tissues, loss of skin elasticity, and sluggishness, loss of firmness and tone, and dermal atrophy. Furthermore, by "signs of skin aging" are also meant enlarged pores, blemishes, discoloration, age spots, keratosis, collagen loss, and other changes in the dermis and epidermis, but also any changes in the external appearance of the skin and keratinous appendages due to aging, such as, for example, surface roughness of the stratum corneum, but also any internal modification of the skin which does not systematically translate into a modified external appearance, such as, for example, thinning of the dermis. By "photo-aging" is meant premature aging of the skin caused by prolonged and cumulative exposure to the sun.

Preferably, the present invention relates to the use of a composition such as described above to improve the barrier function of the skin as well as hydration of the epidermis.

Lastly, a final object of the present invention relates to a cosmetic treatment method, characterized in that a composition comprising an effective amount of the peptide compound according to the present invention is applied topically to the skin or keratinous appendages to be treated, in order to prevent and/or treat signs of skin aging and photo-aging, and to prevent and/or repair the damage caused by UV radiation. In a particular embodiment, the composition is applied prior to exposure of the skin to the sun, and is thus an excellent pre-treatment to prevent damage caused at the DNA level.

In a second embodiment of the present invention, the composition is applied to the skin as after-sun care, to repair any damage caused to the skin at the DNA level.

In a final preferred embodiment of the present invention, the composition is applied either in the morning as an anti-aging daycare, or at bedtime as a night repair care. If applied as a daycare, the composition will provide skin protection with respect to environmental aggressions such as UVB radiation, by limiting the appearance of damage at the DNA level. As a night care, the composition will act by repairing the damage caused to the skin during the day.

The following examples describe and demonstrate the efficacy of peptide compounds such as those described according to the present invention, but should not be construed as limiting the present invention.

FIG. 1 is a histogram showing the results of immunoblotting performed with normal human keratinocytes (NHKs) transfected by means of a siRNA/caspase-14 gene.

FIGS. 2a and 2b are histograms showing the results of 2 comets tests performed on normal human keratinocytes (NHKs) subjected to UV radiation.

EXAMPLE 1

Study of the Expression of Caspase-14 in Normal Human Keratinocytes, in the Presence of Peptide SEQ ID NO: 2

The aim of this study is to determine the expression of caspase-14 in normal human keratinocytes, whether treated or not by means of a peptide according to the present invention:

Protocol:

Cultured normal human keratinocytes, NHKs, were treated with 1% or 3%-peptide SEQ ID NO: 2 for 24 hours. The cells were then washed, fixed with 3.7%-paraformaldehyde using 0.1%-triton in the presence of bovine serum albumin (BSA) (diluted to $\frac{1}{100}^{th}$). The cells were incubated in the presence of a caspase-14-specific mouse monoclonal antibody (BD Biosciences), and then of a secondary antibody, coupled with a fluorescent marker. The cells were then examined by means of an epifluorescence microscope (Nikon® Eclipse E600 microscope).

Results:

An increase was observed in the light intensity in peptide-treated NHK cells with respect to the control conditions. This increase in fluorescence is dose-dependent, since it is greater when the peptide solution is added at 3% than at 1%. Consequently, the peptide SEQ ID NO: 2 activates the expression of caspase-14 in NHKs.

EXAMPLE 2

Study of Caspase-14 Expression by siRNA in NHKs Treated with Peptide SEQ ID NO: 2

In order to quantify the efficacy of a peptide according to the present invention on caspase-14 overexpression in a population of NHKs, the gene coding for caspase-14 was "extinguished" using the siRNA technique.
Protocol:
NHK cells were cultured in 6-well plates up to a confluence of 60% and then treated with 20 µL of 1%-peptide SEQ ID NO: 2. Then, 100 µL of a previously prepared mixture containing the siRNA of caspase-14 and the transfecting agent were carefully added dropwise, on a well per well basis. The cell culture plate was incubated at 37° C. and at 5% $CO_2$ for 72 hours. The culture medium was renewed every 2 days. Four conditions were implemented:
  condition 1: control containing no siRNA nor peptide active ingredient
  condition 2: siRNA-transfected cells, containing no peptide active ingredient
  condition 3: cells that are not transfected but treated with the peptide active ingredient
  condition 4: cells transfected with siRNA, and treated with the peptide active ingredient
The quantification of caspase-14 expression is observed using the conventional immunoblotting technique (Western Blot) carried out by means of an anti-caspase-14 antibody and according to a conventional protocol. To analyze the compensation brought about by the peptide in the NHKs transfected with siRNA, a comparison was performed with respect to non-treated NHKs whose gene had not been extinguished by siRNA.
Results:
Between conditions 1 and 3, the addition of the peptide has been found to lead to a 20.9% increase in caspase-14 protein expression with respect to the control. Between conditions 1 and 2, the effect of siRNA on caspase-14 protein expression is clearly seen: it is 30.6% lower. However, the addition of the peptide SEQ ID NO: 2 to the cells transfected with siRNA helps restore caspase-14, and the decrease due to the presence of siRNA is then only 14% with respect to the control conditions.
In conclusion, the peptide SEQ ID NO: 2 according to the present invention has increased the expression of caspase-14 in NHKs.

EXAMPLE 3

Study of the Expression of Pro/Filaggrin in Human Skin Biopsies in the Presence of Peptide SEQ ID NO: 1

The purpose of this study was to determine the influence of a peptide according to the present invention on the amount of filaggrin and profilaggrin (thereafter pro/filaggrin) in human skin biopsies.
Protocol:
Samples of human skin were cultured at the air/liquid interface. Under a first condition, the samples were treated with the 1% peptide SEQ ID NO: 1 for 24 hours and 72 hours. Under a second condition, the samples were treated with the same peptide but at a concentration of 3% for 24 hours and 72 hours.
These skin samples were thereafter fixed with formaldehyde and then incorporated in paraffin. Sections 2 to 3 µm in size were then made. Immunostaining was carried out after unmasking specific sites by incubation in pepsin. Immunostaining was then performed by means of a filaggrin-specific mouse monoclonal antibody (Tebu Santa Cruz), followed by a secondary antibody, coupled with a fluorescent marker. The skin sections were then examined using an epifluorescence microscope (Nikon® Eclipse E600 microscope).
Results:
An increase in pro/filaggrin staining is observed on the biopsies treated with the peptide according to the present invention. It was noted that not only is staining dose-dependent, but also that it increases with time (between 24 hours- and 72 hours-conditions). It can thus be concluded that the peptide SEQ ID NO: 1 allowed an increase in the cleavage of profilaggrin into filaggrin, through an increase in caspase-14 expression and/or activity.

EXAMPLE 4

Comets Test on NHK Cells

The comets test is a test that allows damage caused to DNA to be quantified at a cellular level.
Protocol:
For this purpose, NHK cells were:
  under condition a: cultured for 24 hours with the peptide compound of sequence SEQ ID NO: 3 at a concentration of 1% and 3%, and then irradiated with UVB radiation at 20 $mJ/cm^2$, in order to observe the protective effect of the peptide active ingredient on the cells;
  under condition b: irradiated, in a first step, with UVB radiation at 20 $mJ/cm^2$, and then treated for 24 hours with said peptide compound at a concentration of 1% and 3%, in order to observe the repairing effect of the active ingredient on the cells.
Control conditions were achieved in each case with no peptide active ingredient present.
The cells were then removed by trypsination from their carrier, and then centrifuged at 900 rpm for 5 minutes before being concentrated and counted.
A specific cell count (25,000 cells) was then incorporated into a 0.75% Low Melting agarose gel, and then deposited on a glass slide previously coated with 1% agarose. The slides were then immersed in a lysis solution for 1.5 hours at 4° C., and then in an alkaline solution for 20 minutes at 4° C. The cells were then lysed and the DNA denatured. The slides were immersed in an electrophoresis solution before applying an electric field (20 V-250 mA). The thus denatured DNA was subjected to migration within an agarose gel at 4° C. Applying a DNA fluorescent dye on the slides (2 µg/ml propidium iodide) allowed the DNA to be observed in the form of comets in those cases where it had been damaged.
Quantification software is used to determine the average Tail Moment applied to each condition being tested. This parameter provides information on the level of DNA damage: the higher it is, the greater the DNA damage.
Results:
The results are shown in FIGS. 2a and 2b. Under condition a, the Tail Moment decreases by 57% when the peptide is applied as a pretreatment (at a concentration of 1% or 3%), that is, the cells have suffered less damage than under the control conditions with UVB radiation. These results clearly confirm the protective effect of the peptide compound of SEQ ID NO: 3 on NHK cells. Furthermore, when the peptide is applied after irradiation without any pretreatment (condition b) the Tail Moment decreases by 31% when the peptide is applied at a concentration of 1%. The Tail Moment decreases by 58% when the peptide is applied at a concentration of 3%. This test under condition b has allowed the remedial role of peptide SEQ ID NO: 3 to be demonstrated on DNA under UV irradiation.

EXAMPLE 5

Demonstration of the Curative Effect of Peptide SEQ ID NO: 2 on Human Skin Biopsies Subjected to UVB Radiation The purpose of this experiment is to measure the repair capacity of a peptide compound according to the present invention after exposure of human skin biopsies to UVB radiation. UV radiation, in particular UVB radiation, induces dimerization reactions that take place on sites comprising two adjacent pyrimidines (thymidine, cytosine). Several types of photoproducts are then formed, among which cyclobutane-pyrimidine dimers, or CPDs. However, it is known that when a cell is subjected to genotoxic stress, its division cycle is temporarily halted to allow DNA repair and avoid the occurrence of mutations within subsequent cell generations. Cell proliferation resumes only thereafter. If the rate or amount of damage is too high, or if the repair is inefficient, the cells trigger a process of programmed cell death, apoptosis. Therefore, immunostaining measurements of the amount of photoproducts formed, by means of an anti-CPD antibody, allow the effectiveness of a compound with DNA-repair action to be evaluated.

CPD Immunostaining Protocol on Skin Biopsies Subjected to UVB Radiation:

Human skin biopsies were cultured at the air/liquid interface. These biopsies were subjected to UVB radiation at 200 mJ/cm$^2$. After irradiation, under a first condition, a 1%-solution of peptide SEQ ID NO: 2 was applied topically to the biopsies for 24 hours. Under a second condition, a 3%-solution of peptide SEQ ID NO: 2 was applied topically for 24 hours. Control conditions are achieved by the topical application of a PBS solution after irradiation.

For staining the cyclobutane-pyrimidine dimers, the skin biopsies were incorporated into paraffin and histological 3 μm thick sections were made. The slides were deparaffinized, hydrated and subjected to immunostaining with an antibody directed against cyclobutane-pyrimidine dimers (MBL D194-1, mouse monoclonal), followed by a suitable secondary antibody (Invitrogen™ A21202), coupled with a fluorescent marker. The skin sections were then examined with an epifluorescence microscope (Nikon® Eclipse E 80i microscope).

Results:

Under control conditions, the observed fluorescence was stronger when the biopsies were subjected to UVB radiation. Under both conditions tested with a post-treatment using peptide SEQ ID NO: 2, much weaker fluorescence was observed than under the control conditions with UVB radiation.

Conclusions:

The peptide SEQ ID NO: 2 provided a better and more significant repair of the damage caused to DNA, in particular as a result of caspase-14 activation. It was also observed that this repair action is dose-dependent since it is more significant when a greater amount of active ingredient is applied.

EXAMPLE 6

Composition of a Sunscreen

| Trade names | INCI Names | wt % |
|---|---|---|
| PHASE A | | |
| Demineralized water | Aqua (Water) | qsp |
| PEMULEN ™ TR1 | Acrylates/C10-30 Alkyl Acrylate Crosspolymer | 0.40 |
| Glycerin | Glycerin | 3.00 |
| NIPASTAT ® Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| PARSOL ® MCX | Ethylhexyl Methoxycinnamate | 7.50 |
| EUSOLEX ® 4360 | Benzophenone-3 | 3.00 |
| PARSOL ® 1789 | Butyl Methoxydibenzoylmethane | 2.00 |
| MYRITOL ® 318 | Caprylic/Capric Triglyceride | 4.00 |
| EMULGADE ® SEV | Hydrogenated Palm Glycerides (and) Ceteareth-20 (and) Ceteareth-12 (and) Cetearyl Alcohol | 5.00 |
| Propylparaben | Propylparaben | 0.15 |
| NACOL ® 16-98 | Cetyl Alcohol | 1.00 |
| PHASE C | | |
| TEA | Triethanolamine | 0.20 |
| PHASE D | | |
| Peptide SEQ ID NO: 3 | | 3 ppm |
| Fragrance | Fragrance | qsp |
| Dye | | qsp |

The invention claimed is:

1. A method of cosmetic treatment, the method comprising:

topically applying onto the skin a composition comprising an effective amount of a peptide compound to repair the damage caused by ultraviolet (UV) radiation, wherein the peptide compound corresponds to one of the following formulas:

Asp-Pro-Ile-Gln-Ala-Cys-Arg-Gly-NH$_2$;   (SEQ ID NO: 1)

Ile-Gln-Ala-Cys-Arg-Gly-NH$_2$;   (SEQ ID NO: 2)

Asn-Arg-Ile-Gln-Ala-Cys-Arg-Gly-NH$_2$; and   (SEQ ID NO: 3)

Pro-Ile-Gln-Ala-Cys-Arg-Gly-Phe-NH$_2$;   (SEQ ID NO: 4)

wherein topically applying includes applying a cosmetically acceptable amount of the composition to activate caspase 14.

2. The method according to claim 1, further comprising, before topically applying, solubilizing the peptide compound in one or more solvents chosen from water, glycerol, ethanol, propanediol, butylene glycol, dipropylene glycol, ethoxylated or propoxylated diglycols, cyclic polyols, or any mixture of such solvents.

3. The method according to claim 1, wherein said effective amount of said peptide compound is at a concentration of between about 0.0005 and 500 parts per million (ppm).

4. The method according to claim 1, wherein the composition further contains at least one other active ingredient selected from the group consisting of vitamins, phytosterols, flavonoids, dehydroepiandrosterone (DHEA), a metalloproteinase inhibitor, a retinoid, an antioxidant agent, a free-radical scavenger, and combinations thereof.

5. The method according to claim 1, wherein topically applying includes applying the composition after exposure to the sun as an after-sun care.

6. The method according to claim 1, wherein topically applying includes applying the composition in the morning as an anti-aging day care, or at bedtime as a night repair care.

7. The method according to claim 1, wherein said effective amount of said peptide compound is at a concentration of between about 0.01 and 5 ppm.

8. The method of claim 1, wherein the composition further comprises a cosmetically acceptable medium.

* * * * *

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION
```

```
<400> SEQUENCE: 1

Asp Pro Ile Gln Ala Cys Arg Gly
1               5

<210> SEQ ID NO 2
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 2

Ile Gln Ala Cys Arg Gly
1               5

<210> SEQ ID NO 3
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 3

Asn Arg Ile Gln Ala Cys Arg Gly
1               5

<210> SEQ ID NO 4
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 4

Pro Ile Gln Ala Cys Arg Gly Phe
1               5
```